US005932717A

United States Patent [19]

Asafov et al.

[11] Patent Number: 5,932,717

[45] Date of Patent: Aug. 3, 1999

[54] METHODS OF OBTAINING DNA-RNA HYBRIDS FROM STURGEON MILT

[76] Inventors: Alexandr V. Asafov, Leninsky prospekt, d.77, korpus 2, kv. 287, Moscow, Russian Federation, 117261; Idia G. Anosova, ul. Jubileinaya, d.88, kv.22, Moskovskaya obl., Khimki, Russian Federation, 141400; Vyacheslav V. Bezjulev, Shipilovsky pr., d.63, korp.1, kv. 490, Moscow, Russian Federation, 115525; Evgenia I. Nesterova, Leninsky prospl. d.22, kv.413, Moscow, Russian Federation, 117334; Likia K. Pashuk, 1 Kolobovsky per., d.15/6, kv.44, Moscow, Russian Federation, 117334

[21] Appl. No.: 08/836,976

[22] PCT Filed: Sep. 29, 1995

[86] PCT No.: PCT/RU95/00216

§ 371 Date: Jul. 25, 1997

§ 102(e) Date: Jul. 25, 1997

[87] PCT Pub. No.: WO96/09832

PCT Pub. Date: Apr. 4, 1996

[30] Foreign Application Priority Data

Sep. 29, 1994 [RU] Russian Federation ............. 94036343

Nov. 9, 1994 [RU] Russian Federation ............. 94041110

[51] Int. Cl.[6] ........................................ C07H 1/00

[52] U.S. Cl. .................. 536/25.3; 536/25.31; 536/25.33; 536/25.34; 536/25.4

[58] Field of Search ................................ 536/23.1, 22.1, 536/25.4, 25.41, 25.42; 514/44

[56] References Cited

U.S. PATENT DOCUMENTS 5,405,775 4/1995 Inouye et al. .

5,708,154 1/1998 Smith et al. .

FOREIGN PATENT DOCUMENTS 9609832 4/1996 WIPO .

*Primary Examiner*—James O. Wilson

*Attorney, Agent, or Firm*—Blank Rome Comisky & McCauley LLP

[57] ABSTRACT

The present invention pertains to DNA-RNA hybrids endowed with immunotropic and antiviral activity, a pharmaceutical preparation made on the basis thereof, and the process for the preparation of said hybrids. Also claimed is a preparation on the basis of DNA endowed with an antiviral activity and a process for the preparation thereof.

2 Claims, No Drawings

METHODS OF OBTAINING DNA-RNA HYBRIDS FROM STURGEON MILT

BACKGROUND OF THE INVENTION

Field of the Invention

The invention pertains to medicine and biology and deals with DNA-RNA hybrids endowed with immunotropic and antiviral activities, the method for the preparation thereof, a pharmaceutical preparation based on the DNA-RNA hybrid as well as preparations on the basis of DNA endowed with the antiviral (including anti-HIV) activity, and methods for the preparation thereof.

There is a known method of preparing the hybrid by mixing DNA and RNA solutions in formaldehyde under definite temperature conditions for analytical purposes. The resulting hybrid possesses no marked biological activity. Moreover, under conditions of a high formaldehyde concentration modification of DNA in primary amino groups may occur (1) which leads to the loss of the specific activity and mutagenicity.

At the present time there are known preparations on the basis of RNA, exogenous DNA as well as nucleotides. The preparation on the basis of RNA-sodium nucleinate is endowed with the leukostimulating and weak immunostimulating activity (2). The preparations based on exogenous DNA have the leukostimulating activity in cytopenia induced by cytostatic therapy (3). Some data are available on the use of nucleotides as antiviral preparations (4).

The limitations of the known preparations on the basis of nucleic acids consist in a narrow range of the pharmacological effect.

There are known methods of achieving the antiviral activity of DNA preparations by modification thereof by means of physico-chemical or chemical treatments.

Thus, there are known methods of DNA modification by complexes with salts of polyvalent metals (5) or EDTA (6). In such physico-chemical method of modification, DNA preparations with molecular weight 300,000–500,000 D are mixed with Fe, Ni, Co, Zn, Mn, Mg salts at a molar ratio of 10–1000:0.5–3.0 (5), or preparations of high molecular DNA are mixed with EDTA (6). The resulting products show the anti-AIDS effect, however, at the same time they have significant cytotoxicity.

There is a known method of enhancing the antiviral activity of DNA by transforming it into apurinic or apyrimidinic acid, that is, DNA derivatives devoid in the former instance of arurinic and in the latter instance of pyrimidinic bases (6).

In accordance with the method (6), arurinic acid is prepared from Na-DNA preparations by thermolysis in an acid medium at pH from 1.5 to 4.0. The resulting products are of oligomeric nature, their molecular weights not exceeding 15–19 kD. Moreover, DNA is known to denaturate under these conditions. Both factors have a negative effect on the biological activity of DNA.

According to the same method (6), apyrimidinic acid is obtained either by alkaline hydrolysis with 0.3 N KOH, or by hydrazinolysis of DNA preparations. It has been established, however, that under these conditions there occur not only denaturation and destruction of the long strand structure but also transformation of purines into derivatives thereof, most likely into hydrazones. Thus, the final compound partially loses purine bases, or purine bases are partially transformed into derivatives. Such compounds cannot be considered to be promising as medicinal preparations since, first, they contain mutations and, second, their composition is not homogeneous, that is, such compounds provide no stable and reproducible pharmacological effect.

DETAILED DESCRIPTION OF THE INVENTION

The above-mentioned shortcomings are lacking in the DNA preparation obtained according to the invention having no cytotoxicity but endowed with higher immunostimulating and antiviral activity.

Preparation of the DNA-RNA Hybrid

The DNA-RNA hybrid according to the invention is a DNA-RNA hybrid sodium salt containing from 0.5 to 5.0% of complementarily bound RNA. The content of the main substance in the product calculated for Na-DNA is at least 80%, that of the protein—not more than 1.5%.

The product is a white powder, well soluble in water and physiological saline solution.

The hybrid structure of the final product has been confirmed by tests with RNAse (7).

For the preparation of the hybrid, the final product from sturgeon milt obtained by the known method (8), before precipitation in alcohol is additionally incubated for 20–90 min at a pressure of 1.5–2 excessive atmosphere, a temperature of 105°–115° C. and pH from 8.5 to 9.0. Then the pressure is released, pH is adjusted to 5.5–7.5 and the solution is incubated at 55°–60° C. for 1–4 hours after which the product is recovered by precipitation followed by multiple washings with alcohol.

Determination of the anti-HIV Activity of the Claimed DNA-RNA Hybrid

The continuous human lymphoblast cell line H9 in a concentration of $0.3 \times 5 \times 10^6$ cells/ml was used. The cells were propagated in RPMI-1640 medium with 15% inactivated calf embryo serum, 300 μg/ml J-glutamine, 100 μg/ml gentamycine, 10 mM HEPES-buffer, and grown in suspension.

The HIV-infected cell line H9/IIIB was cultivated in a similar way.

The number of cells expressing HIV antigens was determined by the method of Coons, A. H. (J. Exp. Med., 1985, vol. 102, p. 49) using the serum from an AIDS patient containing antibody to HIV.

The cells were infected with a concentrate of the culture fluid of H9/IIIB cell culture obtained by centrifugation of the material in 20% sucrose gradient at 24,000 rpm.

The inhibiting effect of the claimed substance on HIV replication was determined in a suspension of continuous lymphoblastoid line of H9 cells.

The cells were separated from the culture fluid by centrifugation at 100 rpm for 10 min and then resuspended at a concentration of $5 \times 10^5$ cells/ml in a fresh nutrient medium containing different doses of the substance tested.

Before the addition of the said substance to the cell culture the cells were infected with HIV. The cells were washed three times with pure RPMI-1640 culture by centrifugation at 1000 rpm for 10 min. The resulting cell sediment was resuspended in the growth medium and incubated for 72 hours at 37° C.

At the end of the incubation period the cells were separated from the culture fluid by the same centrifugation regimen, and the presence of the virus-specific antigen in them was determined by immunofluorescence technique (IF). the Results of these studies are presented in Table 1.

TABLE 1

The effect of DNA-RNA hybrid on the species-specific antigen expression

| Experimental conditions | Percent of fluorescent cells in immuno-fluorescence test: 5 days | 7 days |
|---|---|---|
| Uninfected cells | 2.2 | 1.9 |
| HIV-infected cells | 50.1 | 34.5 |
| RNA* | | |
| 10/ug/ml | 10.0 | 11.2 |
| 50/ug/ml | 5.3 | 5.1 |
| 100/ug/ml | 2.4 | 2.5 |
| 150/ug/ml | 2.5 | 2.3 |
| 200/ug/ml | 1.5 | 1.6 |
| DNA-RNA hybrid | | |
| 10/ug/ml | 12.0 | 13.0 |
| 50/ug/ml | 21.0 | 41.0 |
| 100/ug/ml | 25.0 | 39.0 |
| 150/ug/ml | 18.2 | 14.9 |
| 200/ug/ml | 11.8 | 16.1 |

*Data presented according to (9).

It will be seen from the Table that the DNA-RNA hybrid of the invention in the range of concentrations from 50 to 100 μg/ml exerted antiviral effect on HIV virus exceeding that of RNA.

Investigation of the Immunological Activity of DNA-RNA Hybrid

1. The effect on allergic reactions of the delayed type

The effect of the claimed preparation to lymphocyte blastogenic response (LBR), spontaneous and PHA-stimulated was examined. The conventional method reported by M. M. Averbakh (10) was used. for the preparation of lymphocyte cultures. The preparation tested was added to the cultures in different concentrations and the cultures were kept in the thermostate for 4 days (11). The transformed cell counts were done under the microscope and LBR was expressed in %. The results of the study are presented in Table 2.

TABLE 2

| Concentration of the test preparation/ ug/ml | Lymphocyte blastogenic response (%) — Control: Lymphocyte culture without the addition of DNA-RNA hybrid — Spontaneous | Control — PHA-stimulated | Experiment: Addition of DNA-RNA hybrid — Spontaneous | Experiment — PHA-stimulated |
|---|---|---|---|---|
| 10 | | | 2.1 ± 0.18 | 3.2 ± 0.21 |
| 50 | | | 1.1 ± 0.12 | 2.4 ± 0.19 |
| 100 | 0.13 ± 0.09 | 3.8 ± 0.92 | 4.8 ± 0.51 | 9.5 ± 0.43 |
| 150 | | | 4.9 ± 0.49 | 9.9 ± 0.48 |
| 200 | | | 3.1 ± 0.31 | 7.8 ± 0.51 |

It will be seen from the above Table that the tested preparation showed the immunostimulating effect, enhancing both spontaneous and PHA-stimulated LBR.

2. The effect on virus growth

TABLE 3

| | | % of virus growth inhibition (mean) |
|---|---|---|
| Influenza virus | Chick embryo cell culture | 69% |
| Adenoviruses | HeLa cell culture | 72% |
| Herpes viruses | HEp-2 cell culture | 89% |

It will be seen from the above data that the preparation obtained by the claimed method is capable of inhibiting virus growth being effective with influenza viruses, adenoviruses, and herpes viruses.

The results of the investigations of anti-HIV activity, the effect on the expression of the species-specific antigen and virus growth as well as of the immunologic activity attest to the fact that the DNA-RNA hybrid according to the invention is endowed with the immunostimulating and antiviral effect (effective against HIV, influenza, herpes and adenoviruses).

A new pharmaceutical preparation was developed on the basis of the DNA-RNA hybrid obtained by the method described above.

The pharmaceutical preparation contains the DNA-RNA hybrid and a pharmaceutically acceptable solvent at the following ratio of the components (in % by weight):

| | |
|---|---|
| DNA-RNA hybrid | 0.5–5.0% |
| Pharmaceutically acceptable solvent | up to 100.0 |

The preparation is made by dissolving the hybrid prepared by the claimed method in distilled water or physiological solution followed by filtration. The preparation is a transparent solution with the shelf life up to 2 years.

Below are presented the results of experimental investigations of pharmacological properties of the pharmaceutical preparation obtained on the basis of the DNA-RNA hybrid.

TABLE 4

The effect of the pharmaceutical preparation based on the DNA-RNA hybrid on the population of T-cells in patients with HIV infection

| Stages of treatment | T-cell population (mean values): T-helpers | T-suppressors | Th/Ts |
|---|---|---|---|
| AIDS patients | 25.5 | 37.2 | 0.67 |
| After treatment with the claimed preparation | 39.2 | 27.8 | 1.41 |

It will be seen from the above Table 4 that the administration of the preparation normalizes the Th/Ts ratio which is a positive prognosis sign in AIDS and AIDS-associated syndrome.

Subsequently, the immunotropic effect of the preparation was investigated in experiments in vivo.

The preparation under study was administered to intact rabbits once or during one week. Lymphocyte blastogenic response, spontaneous and PHA-stimulated, was examined. The results of the experiment are presented in Table 5.

TABLE 5

The dynamics of the immunological parameters after administration of the claimed preparation in experiments in vivo

| REGIMEN of the preparation administration | Lymphocyte blastogenic response (%) | |
|---|---|---|
| | Spontaneous | PHA-stimulated |
| Single administration | 4.2 ± 0.94 | 11.2 ± 0.99 |
| Course administration | 5.9 ± 0.53 | 19.4 ± 0.82 |
| Control | 0.12 ± 0.001 | 3.1 ± 0.89 |

Thus, it will be seen from the above Table that the claimed preparation enhanced the immunity in the experiments in vivo.

The Process for Obtaining a DNA Preparation

The claimed process for obtaining the DNA preparation according to the invention comprises homogenization of sturgeon milt tissue from which fat and membranes had been removed in the standard citrate-salt solution, detergent deproteinization with dodecyl sulphate and salt denaturation of proteins released from DNA, followed by dosed ultrasonic degradation of high-polymer DNA in the air atmosphere at a temperature of 10°–18° C. in the presence of special additives. Further, the DNA preparation is separated by the conventional method from biogenic and non-biogenic admixtures using sorbents and the membrane technology. The purified preparation is precipitated with alcohol and dried. The final preparation has the following characteristics:

Molecular weight from 66 to 500 kD;

RNA content from 3.0 to 5.0%;

Protein content from 0.7 to 1.5%;

Content of metals of variable valency not exceeding 0.001%;

N/P ratio from 1.0 to 1.5.

The special additives introduced at the stage of ultrasonic treatment comprise one- two- or three-component systems selected from the following groups of substances:

The component "A" may be represented by peroxides, hydroperoxides, diazoamino compounds, chlorates, chromates, permanganates used in amounts of from 0.005% to 0.05% of the milt weight. Component "A" is used only in combination with component "B" or "B"+"C".

The component "B" may be represented by carbohydrates such as fructose, glucose, sorbose or compounds of such classes as sulphates, thiosulphates, oxyacids, oxyaldehydes and other compounds with the reducing capacity (for example, pyrogallol, sulphoxylate, etc.) added in an amount equimolar to that of component "A" in two- or three-component systems, or in an amount of from 0.1 to 1% of the weight of milt in one-component additive system.

The component "B" is represented by microamounts of salts of metals of variable valency in an oxide or lower oxide ionic form or in the form of complex salts. Their concentration in the system must be from 0.1% to 0.0001% of the molar concentration of component "A". When such amounts of variable valency metals are added to the reaction mass with the raw material (milt, sodium chloride, etc.) no addition of component "B" is required.

Treatment of the DNA-containing biogenic reaction mass with the said systems of chemical agents under conditions of ultrasonic degradation in air at a temperature of 10°–18° C. permits under mild conditions to break glycoside bonds in nucleotides and obtain compositionally homogeneous native polymers with the stable properties.

The resulting preparation comprises a white powder with a creamy tint endowed with a high antiviral activity, low toxicity and stable analytical characteristics.

Below, the results of experimental and clinical investigations of toxicity and antiviral activity of the DNA preparations obtained by the claimed method are presented.

Investigation of Toxicity of the Preparations Under Conditions of Acute and Chronic Experiments The preparations obtained by the claimed method (in accordance with examples 5–9) were evaluated by the method of Gatsuro (12): examinations of behaviorial reactions, neuromuscular excitability, vegetative reflexes under conditions of acute and chronic inoculations. Mice were inoculated with preparations in doses of 0.1–10 mg/kg in a volume of 0.2–0.5 ml. The animals were observed for 240 min after inoculation, their conditions being recorded every 10 min. The observations were evaluated by an 8 score system.

The evaluation of the behaviorial reactions throughout the observation period showed the standard motor activity, excitability and reactivity within normal limits. The orientation reflexes were without changes. No tremors, convulsions, gait disorders or changes in muscle tone were observed. Corneal and pupillary reflexes, respiration rate and heart rate were within the limits of physiological norm.

In studies of chronic toxicity the preparation was administered to the animals for 21 days followed by pathoanatomical examination of the internal organs stained with hematoxylin-eosin and sudan III.

The examinations revealed normal blood filling of the organs, no hemorrhages in the organs were detected. The weight of the liver was within normal limits; no signs of hepatogenic intoxication, i.e. atrophy, cell vacuolation, polymorphism, picnosis were found. Thus the presented data attest to the lack of toxicity in the preparations obtained by the claimed method.

Investigation of the Antiviral Activity, anti-HIV Activity and Cytotoxicity of the DNA Preparations Obtained by the Claimed Method The cells.—A continuous lymphoblast line of MT-4 cells was used in the study. The cells were propagated in a concentration of $0.2\times10^6$ cells/ml in RPMI-1640 medium with 15% fetal calf serum, 300 $\mu$g/ml L-glutamine and 100 $\mu$g/ml gentamycine. The cells were cultivated in suspension in 24-well plates of NUNCLON Company.

The viability of the cells was determined by staining with 0.4% trypan blue.

The preparations: azidothymidine in a concentration of 5 $\mu$g/ml was used as the control, and 5 preparations obtained by the claimed method were used in the form of a solution with the substance concentration of 5 $\mu$g/ml.

Cytotoxicity of the preparations was determined in 24-well plastic plates. Each well of the panel was filled with 1 ml of cell suspension in a concentration $0.2\times10^6$ cells/ml after which to different wells various doses of chemopreparations were added: 1600, 1000, and 400 $\mu$g/ml. After treatment of the cells with the chemopreparations the panels with the cells were placed into a thermostat and incubated at 37° C. in an atmosphere of 5% $CO_2$ and 98% humidity for 3–5 days. At the end of this term the results were read by the number of live and dead cells in the individual wells of the plate.

The formation of syncytium was determined by counting of syncytial cells in the infected cultures containing or not containing the preparations under study.

Also, human continuous lymphoblast cell line H9 in a concentration of $0.3\times5\times10^6$ cells/ml was used. The cells were cultivated in RPMI-1640 medium with 15% inactivated calf embryo serum, 300 μg/ml L-glutamine, 100 μg/ml gentamycine, 10 mM HEPES-buffer and grown in suspension.

In a similar way, HIV-infected cell line H9/III B was cultivated.

The preparations obtained by the claimed method were used in concentrations of 1600, 1000, 400 μg/ml.

Immunofluorescence. The number of cells expressing HIV-antigen was determined by the method of Coons, A. H. (J. Exp. Med., 1955, vol. 102, p. 49) using the sera from an AIDS patient containing antibodies to HIV.

Virus.—The cells were infected with a concentrate of the culture fluid from H9/III B cell culture obtained by centrifugation of the material in 20% sucrose gradient at 24,000 rpm.

In order to determine the inhibiting effect of the DNA preparations on HIV replication, the cells of H9 line were separated from the culture fluid by centrifugation at 1000 rpm for 10 min, resuspended in a concentration of $5\times10^5$ cell/ml in a fresh nutrient medium containing various doses of the DNA preparations. The cells were left for contact with the preparation for 1½ hrs at 37° C. At the end of the incubation period the cells were separated from the culture fluid, and the presence of the virus-specific antigen was determined by immunofluorescence technique.

The Cytotoxic Effect of DNA Preparations

The studies demonstrated that the preparations of different lots in the doses tested exerted no toxic effect on the cells. The results of the studies are presented in Table 6. It will be seen from this Table that the investigated preparations of all the lots obtained by the claimed method exhibited no cytotoxicity in the MT-4 cell system.

TABLE 6

Comparative cytotoxicity of the preparations obtained by the claimed method in MT-4 cell culture

| Preparation (obtained according to example No.) | Preparation concentration/ ug/ml | MT-4 cell viability indices: % of live cells | Cell concentration per ml × $10^6$ | Proliferation index |
|---|---|---|---|---|
| 5 | 1600 | 89.2 | 0.39 | 1.80 |
| | 1000 | 99.4 | 0.41 | 1.99 |
| | 400 | 100.0 | 0.52 | 2.40 |
| 6 | 1600 | 89.8 | 0.35 | 1.89 |
| | 1000 | 91.7 | 0.41 | 2.00 |
| | 400 | 99.8 | 0.51 | 2.60 |
| 7 | 1600 | 89.2 | 0.39 | 1.80 |
| | 1000 | 99.5 | 0.49 | 2.00 |
| | 400 | 100.0 | 0.52 | 2.60 |
| 8 | 1600 | 100.0 | 0.42 | 1.80 |
| | 1000 | 100.0 | 0.49 | 2.40 |
| | 400 | 100.0 | 0.53 | 2.60 |
| 9 | 1600 | 100.0 | 0.45 | 1.85 |
| | 1000 | 100.0 | 0.48 | 2.20 |
| | 400 | 100.0 | 0.54 | 2.60 |
| Azidothymidine | 5 | 17.5 | 0.16 | 1.0 |
| Cell control | — | 100.0 | 0.56 | 2.80 |

The Antiviral Effect of the DNA Preparations on the Model of III B HIV-1 Strain The determinations of the presence of syncytial cells in the control and experimental cultures showed that while in the control cultures without the addition of the preparations under study the number of cells was 800±100 per well, in the well containing the preparations there were either no syncytial cells or they were detected in low numbers. The results are presented in Table 7.

TABLE 7

The effect of the preparations obtained by the claimed method on syncytial cells

| Preparation obtained in accordance with example | Number of syncytial cells in the culture |
|---|---|
| 5 | 2 |
| 6 | — |
| 7 | 4 |
| 8 | — |
| 9 | — |
| Control | 800 ± 100 |

The Antiviral Effect on H9 Cell Line Infected with HIV

In the concentrations tested, the DNA preparations obtained by the claimed method were demonstrated to exert an antiviral effect on human immunodeficiency virus (HIV). The results of this series of experiments are presented in Table 8.

It will be seen from the materials of Table 8 that said DNA preparations exert a marked antiviral effect in HIV-infection demonstrating no cytotoxicity at that.

TABLE 8

The effect of DNA preparations on the expression of the species-specific antigen in H9 cells infected with HIV

| Preparations obtained in accordance with example | Concentration of the preparation, /ug/ml | Percent of fluorescent cells in the immunofluorescence test: 5 days | 7 days |
|---|---|---|---|
| 5 | 1600 | 2.4 | 2.5 |
| | 1000 | 3.8 | 3.4 |
| | 400 | 5.3 | 5.1 |
| 6 | 1600 | 2.2 | 2.1 |
| | 1000 | 4.3 | 4.2 |
| | 400 | 5.1 | 5.0 |
| 7 | 1600 | 2.85 | 2.6 |
| | 1000 | 3.99 | 3.3 |
| | 400 | 5.5 | 5.2 |
| 8 | 1600 | 3.1 | 3.0 |
| | 1000 | 4.5 | 4.0 |
| | 400 | 5.4 | 5.3 |
| 9 | 1600 | 2.95 | 2.8 |
| | 1000 | 3.8 | 3.6 |
| | 400 | 5.2 | 5.2 |
| Control of uninfected cells | | 2.2 | 1.6 |
| Control of infected cells | | 54.8 | 45.9 |

Investigation of the Antiviral Activity of the DNA Preparations in Accordance with the Invention Against Influenza Virus, Adenoviruses and Herpes Viruses The antiviral effect of the preparations obtained by the claimed method was tested in special experiments using the standard methods. The results are presented in Table 9.

TABLE 9

The antiviral activity of the DNA preparations obtained by the claimed method

| Virus | Experimental method | % of virus growth inhibition. Preparation obtained according to examples 5 | 6 | 7 | 8 | 9 |
|---|---|---|---|---|---|---|
| Influenza virus | Chick embryo cell culture (Krug, R. M., Cell, 1979, 18: 329) | 41.0 ± 2.9 | 39.9 ± 4.8 | 50.1 ± 9.8 | 61.0 ± 1.9 | 54.1 ± 2.5 |
| Adenoviruses | HeLa cell culture (Wigand, R. et al. Intervirology, 1982, 18:169) | 44.8 ± 3.9 | 51.9 ± 6.1 | 55.3 ± 9.0 | 49.0 ± 2.9 | 63.1 ± 5.9 |
| Herpes viruses | HEp-2 cell culture (Allen, C. P. Aust. J. Vet. Res., 1983, 44: 263) | 39.0 ± 1.2 | 44.8 ± 6.4 | 51.9 ± 1.9 | 54.0 ± 2.6 | 55.2 ± 6.1 |

Thus, it will be seen from the above Table that the preparations obtained by the claimed method exhibit a wide spectrum of antiviral activity comprising both anti-HIV activity and inhibition of viruses of other classes.

The invention is illustrated by the following examples.

EXAMPLE 1

1.2 kilo of freshly frozen sturgeon milt is ground and homogenized in 2 liters of a citrate-salt solution consisting of 0.15 M sodium chloride and 0.0021 M sodium citrate at room temperature. The resulting homogenate is poured into a reactor containing 34 l of the citrate-salr solution. Then, 4 l of 6% sodium dodecylsulphate solution in 45% solution of rectified ethyl alcohol (240 g in 4 l of 45% alcohol) are added. The resulting reaction mixture is heated for 1–1½ hours up to 60°–65° C. and are kept at this temperature for 1–1½ hours being mixed with an anchor mixer, after which time to the solution are added 40 l of 5 M sodium chloride solution and mixed for 1½ hours. Then the resulting reaction mass is cooled to 12°–16° C., mixed with kieselguhr at a ratio 10:1 using a mixer and filtered in a Nutch-filter.

The resulting filtrate of high polymer DNA in 2.5 l aliquots is concentrated by electrodialysis in a multi-chamber apparatus-electrodialyser of the filter-press type comprising alternating membranes of MA-40 and MK-40 types with intermediate coils of rubberized asbestos fabric and separators-turbulators. The cathode is a plate of stainless steel of the quality XI8HI0T with the working surface of 4 $dm^2$, the anode is a platinized titanium of the same surface. The electrodialyzer consisted of 7 "demineralization" chambers and 8 "concentration" chambers as well as two electrode chambers. The working surface of each membrane was 4 $dm^2$.

The reaction mass of the high-polymeric DNA was pumped with a pump through the "demineralization" chambers of the electrodialyser at a linear rate of 2.3 cm/s, while at the same time through the "concentration" chambers 0.5% sodium chloride solution was pumped, and through the electrode chambers tap water was pumped. Constant current was conducted through the electrodialyser at a temperature of 15°–20° C. the current strength corresponding to the current density of 1.5 $A/dm^2$. In the course of electrodialysis pH of the solution was maintained within the range of 6.5–7.5 by the addition of diluted hydrochloric acid (1:3). The temperature in the course of electrodialysis was maintained by supplying cooled water into the coils (pipes) of the intermediate capacities. The process of electrodialysis concentration yields 1.2 l of high-polymer DNA. The duration of the process is 4 hours, the specific output of the apparatus is 1.0 $l/m^2$×hour, and the power intensity of the process is 216 Wt/hout/liter. At that, the current efficiency is 70.0%. The concentrated solution of the high-polymeric DNA is poured into a magnitostrictor module and ultrasonicated for 45 min after which it is filtered three times in an apparatus "BIOKON". Further, the product is incubated for 20 min at a pressure of 1.5 excess atmosphere, a temperature of 105° C., pH 8.5, the pressure is gradually thrown off and incubation is further conducted at 55° C. and pH 5.5 for 1 hour. Then the product is precipitated with alcohol, the precipitate is collected by centrifugation, washed with 95% alcohol and dried.

The resulting white powder has been analysed. It is a DNA-RNA hybrid sodium salt containing 0.5 complementary bound RNA. The content of the main substance in the product as recalculated for Na-DNA is 80%, the protean content is 0.5%.

The hybrid structure of the obtained product was confirmed by tests with RNAse.

Pharmacological and virological investigations revealed the immunotropic and antiviral activity of the preparation against a number of viruses (HIV, adenoviruses, herpes virus, influenza virus).

EXAMPLE 2

1.2 kg of freshly frozen sturgeon milt is ground and homogenized in 2 l of citrate-salt solution consisting of 0.15

M sodium chloride and 0.0021 M sodium citrate at room temperature. The resulting homogenate is poured into a reactor containing 34 l of the citrate-salt solution. Then 4 l of 6% sodium dodecylsulphate solution in 45% solution of rectified ethyl alcohol (240 g in 4 l of 45% alcohol). The resulting mass is heated for 1–1.5 hours up to 60°–65° C. and mixed with an anchor mixer for 1.5 hours. Then 40 l of 5M NaCl solution are added and mixed for 1.5 hours. The resulting mass is cooled to 12°–16° C., mixed with kieselguhr in a ratio of 10:1 and filtered in Nutch-filter.

The resulting filtrate of high polymer Na-DNA is concentrated in chambers of an electrodyalizer. After that the solution is poured into a magnitostrictor module and sonicated for 40 sec. after which it is filtered through a Millipore filter until a transparent solution is obtained and then concentrate 3-fold in a "BIOKON" apparatus.

The product is further incubated for 90 min at a pressure of 2 excess atmospheres, a temperature of 115° C. and pH 9.0, then the pressure is thrown off and the product is incubated at 60° C., pH 7.5 for 4 hours. Then the product is precipitated with alcohol, the precipitate is collected by centrifugation, washed with 96% alcohol and dried.

The resulting white powder is a DNA-RNA hybrid sodium salt containing 5.0% complementary bound RNA. The content of the main substance in the product as recalculated for Na-DNA is 90%, the protein content is 1.5%. The hybrid structure of the resulting product was confirmed by tests with RNAse.

The immunological and virological studies revealed the immunotropic and antiviral activity of the preparation against a number of viruses (HIV, adenoviruses, herpes virus, influenza virus).

EXAMPLE 3

For obtaining a pharmaceutical preparation, 0.5 g of the substance prepared by the claimed method was dissolved in 99.5 ml of distilled water or physiological saline solution. The resulting preparation is a transparent fluid.

The preparation was investigated for the anti-HIV and immunotropic activity.

When the preparation was administered to HIV-infected patients, the prognostic index—the Tx/Tc ratio—improved, increasing from 0.67 to 1.41.

In the experiments in vivo, a single administration of the preparation led to an increase in the values of spontaneous and PHA-stimulated LBR. Thus, after a single administration the spontaneous LBR increased from 0.11 to 3.8 and after a course administration from 0.11 to 4.2. The PHA-stimulated LBR increased from 3.0 to 10.9 after a single administration and to 18.9 after multiple doses.

Thus, this example illustrates the immunotropic and antiviral activity of the preparation.

EXAMPLE 4

To prepare a pharmaceutical preparation, 6.0 g of the substance obtained by the claimed method and containing the DNA-RNA hybrid were dissolved in 94.0 ml of distilled water or physiological saline solution. The preparation is a transparent fluid with a shelf life of 2 years.

The preparation was tested for anti-HIV and immunotropic activity.

When the preparation was administered to HIV-infected patients, the prognostic index—the Tx/Tc ratio—improved, increasing from 0.62 to 1.42.

In the in vivo experiments a single administration of the preparation to rabbits led to an increase in the values of spontaneous and PHA-stimulated LBR. Thus, after a single administration spontaneous LBR increased from 0.12 to 3.4 and after a course administration from 0.15 to 4.8. The PHA-stimulated LBR increased from 3.1 to 11.2 after a single administration and to 20.1 after a course administration.

Thus, this example illustrates the immunotropic and antiviral activity of the claimed preparation.

EXAMPLE 5

1.2 kg of frozen sturgeon milt from which fat and membranes had been removed before freezing were thawed to +2° C. and treated into a mince which was homogenized in 2.0 l of the standard citrate-salt solution for 3–5 min at 800–1000 rpm. The homogenate was placed into a 100 l capacity apparatus to which 34 l of the standard citrate-salt solution and 4 l of 6% sodium dodecylsulphate were added and, with uninterrupted stirring was heated to 60° C. and incubated at this temperature for 1–1½ hours. After this time, with the stirring continued, 40 l of 23% solution of sodium chloride are added, and the mixing continued for another hour at 60° C. At the end of this time the reaction mixture is cooled to 2°–5° C. and transferred to an ultrasonication apparatus. Ultrasonication is carried out in open baths of 10 l capacity. For this treatment, the bath is filled with 5 l of the reaction mixture to which are added 0.1 l of aqueous solution of isopropylbenzole hydroxide in a concentration of $2.5\times10^{-4}$ mol/l, 0.1 l of freshly prepared aqueous solution of dioxymaleic acid in a concentration of $2.5\times10^{-4}$ mol/l and 10 l of Mohr's salt in a concentration of $2.5\times10^{-7}$ mol/l prepared by the method of sequential dilution of more concentrated solutions. Sonication treatment is carried out for 10 min at a temperature of 18° C. and current frequency of 750 HGc and intencity of 8–10 wt/cm$^2$. At the end of the sonication treatment the solution is tranferred to a mixer wherein all ultrasonicated portions are combined, mixed with 5 kg of kieselguhr, kept for 15 min and then are supplied for filtration on a Nutch-filter. The filtered solution of the final product is additionally purified and concentrated by ultrafiltration on separation columns with hollow fibers.

From the purified solution, the final product is precipitated with 70% ethanol, subjected to multiple washings with ethanol with changing (decreasing) concentration of water, separated from the liquid phase and dried. Thus, preparation No.1 is obtained containing 3.25% RNA, 0.9% protein, less than 0.001% iron, N/P ratio 1.3, and molecular weight 460 kD.

The experiments on the determination of acute and chronic toxicity in vivo demonstrated the preparation to be nontoxic. In MT-4 cell cultures treated with the preparation no cytotoxicity was demonstrable. The preparation manifested antiviral effect on the model of the III/B HIV-1 strain, and was found effective against influenza, herpes, and adenoviruses.

EXAMPLE 6

The final product was prepared by the methods described in Example 5, with the exception of the sonication procedure: to the bath containing 5 l of the reaction mixture were added 40 ml of 0.1% hydrogen peroxide solution and a solution of 0.2 g ascorbic acid in 1 liter of water. The sonication was carried out for 30 min at a temperature 8°–10° C. with the above-mentioned parameters of US-generator.

The resulting preparation No.2 has molecular weight 340 kD, the RNA content 5.0%, protein 1.5%, iron less than 0.001%, N/P ratio=1.0. The preparation is nontoxic in the experiments in vivo and in MT-4 cell culture, and exhibited antiviral activity against strain III HIV-1, herpes viruses, influenza and adenoviruses.

EXAMPLE 7

The final product was obtained in the same way as described in Example 5 with the exception of the sonication procedure: to the bath containing 5 l of the reaction mass were added 0.75 g glucose in 1 liter of water. The sonication was carried out at a temperature of 15° C. for 1 hour at the generator parameters described in Example 1. The resulting preparation No.3 has molecular weight 500 kD, N/P ratio 1.5, the content of RNA 4.7%, protein 1.3%, iron less than 0.001%. It was shown to be non-toxic in the experiments in vivo and in HT-4 cell culture, and to exhibit antiviral activity for HIV-1, herpes, influenza and adenoviruses.

EXAMPLE 8

The final product was obtained in the same way as described in Example 7, however, instead of glucose solution, 0.08 g of sodium sulphide solution in 100 ml of water were added. The resulting preparation No.4 has molecular weight 300 kD, the content of RNA 4.0%, protein 1.0%, iron less than 0.001%. It was shown to be non-toxic in experiments in vivo and in MT-4 cell culture and to exhibit antiviral activity for the III-B strain of HIV-1, influenza, herpes and adenoviruses.

EXAMPLE 9

The final product was obtained in the same way as described in Example 5, however, at the stage of sonication to the system were added 0.1 liter of aqueous solution of isopropyl benzene hydroperoxide in a concentration of $2.5\times10^{-3}$ mol/l, 0.1 liter of freshly prepared ascorbic acid solution in a concentration $2.5\times10^{-3}$ mol/l, and 1.0 l of iron dichloride solution in a concentration of $2.5\times10^{-8}$ mol/l obtained from more concentrated solutions by successive dilutions. The resulting preparation No.5 has molecular weight 300 kD, N/P ratio 1.0, the content of RNA 3.0%, protein 0.7%, iron less than 0.001%. It was demonstrated to be nontoxic in experiments in vivo and in MT-4 cell culture and to exhibit antiviral activity for HIV-1, influenza, herpes, and adenoviruses.

REFERENCES

1. Obolenskaya, M. Yu.—Hybridization of nucleic acids in formamide solutions with high concentration. Molecular biology. Kiev, 1982, issue 31, p. 27–32
2. Rychnev, V. E.—Nucleic acids and their therapeutic application. Vrachebnoe Delo, 1981, No. 8, p. 114–118
3. Soboleva, E. P. Use of DNA in cytopenia induced by myelosan. Bull, Exp. Biol. Med., 1976, v. 81, No. 4, p.409–411
4. $IPC^4$ A61K 31/66, 31/665. PCT (0). International application No. 89/04662
5. $IPC^5$ A61K 31/70, A61K 9/08, PCT (0), international application No. 93/10794.
6. $IPC^4$ A61K 31/70, C07N 21/04, FRG (DE) Application No. 0 37 24951, published Feb. 9, 1989
7. Molecular biology. Kiev, 1979, p. 45–55
8. Spigelman, S. Hybrid nucleic acids., Patent RF No. 2017496
9. Fundamental and applied problems of AIDS. Collected Research papers, M., 1988
10. Averbakh, M. M.—Enhanced delayer type sensitivity and the infectious process. M., "Medizina", 1974
11. Nowell, P. C.—Cancer Res., 1960 vol. , p. 462–466
12. Gatsuro, V. V.—A method for primary pharmacological testing of biologically active substances. M., 1974.

We claim:

1. A process for the preparation of a DNA-RNA hybrid having high immunotropic and antiviral activity comprising the steps of:

(a) homogenizing a cell material obtained from a sturgeon milt;

(b) treating said homogenate with a detergent;

(c) precipitating a said hybrid from said treated homogenate; and (d) purifying and recovering the purified said hybrid from said homogenate.

2. The process of claim 1, further including the steps of:

(e) incubating said hybrid for about 20–90 minutes at a pressure of about 1.5–2.0 atm, a temperature of at least 105°–115° C. and a pH of about 8.5–9.0;

(f) lowering the pressure; and (g) incubating said recovered product for about 1–4 hours at a temperature of about 55–60° C. and a pH of about 5.5–7.5, followed by precipitation and washing with alcohol.

* * * * *